US005552601A

United States Patent [19]
Beall

[11] Patent Number: 5,552,601
[45] Date of Patent: Sep. 3, 1996

[54] METHOD OF DRYING CELLS FOR SCANNING ELECTRON MICROSCOPY

[75] Inventor: Hie P. Beall, Durham, N.C.

[73] Assignee: Duke University, Durham, N.C.

[21] Appl. No.: 274,629

[22] Filed: Jul. 13, 1994

[51] Int. Cl.$^6$ .................................................. H01J 37/18
[52] U.S. Cl. ................................................................ 250/307
[58] Field of Search ..................................... 250/306, 307, 250/310, 311, 304

[56] References Cited

U.S. PATENT DOCUMENTS

| | | | |
|---|---|---|---|
| 4,727,029 | 2/1988 | Mori | 250/307 |
| 5,352,898 | 10/1994 | Mehta | 250/307 |

OTHER PUBLICATIONS

Bozolla, J. J. and Russel, L. D. *Electron Microscopy*, Jones & Barlelett Publishers, Boston, (1992).
Cohen, A. L., *Scanning Electron Microscopy* (1979).
Material Data Sheet (Jan., 1991) from Peldri II Ted Pella, Inc. Catalog No. 1240, 1242.
3M Industrial Chemical products Division "Advanced Vapor Degreasing" (Dec., 1992).
Catalog page "Typical property Comparisons for 3M Performance Fluids" (Nov., 1992) from 3M Industrial Chemical Products Division.
Sales Brochure "PF–5050, A No Ozone–Depleting Alternative to CFCs" (Aug., 1991) from 3M Industrial Chemical Products Division.
Material Safety Data Sheet (May, 1994) from Aldrich Chemical Co., Inc.
Material Safety Data Sheet (Dec., 1993) 3M Specialty Chemicals Division.
Publication by 3M Industrial Chemical Products Division "Liquid Burn–In Testing with Fluorinert ™" (Apr., 1993).
Dey, et al., *Journal of Microscopy*, vol. 156, Pt. 2 pp. 259–261 (Nov., 1989).
Catalog page from Aldrich Chemical Company, Inc. (1994) pp. 546, 763, 1332.

*Primary Examiner*—Jack I. Berman
*Assistant Examiner*—Kiet T. Nguyen
*Attorney, Agent, or Firm*—Richard E. Jenkins

[57] ABSTRACT

A method for preparing biological specimens, such as cells and soft tissues, for electron microscopy, preferably scanning electron microscopy. The method is free of detrimental effects on the protective ozone layer of the earth, as the method comprises air drying the specimens with a fluorinated carbon fluid that has an ozone depletion potential of 0. Suitably, the fluorinated carbon fluid is also inert, thereby obviating any potential health hazards to the technicians performing the method and other nearby persons. The fluorinated carbon fluid employed needs to have a fairly low surface tension, less than about 10 dynes/cm at 25° C., and a fairly low boiling point, less than 35° C., so that the material will readily evaporate from the specimen via air drying. A suitable material is the perfluorinated carbon fluid of the empirical formula, $C_5F_{12}$.

15 Claims, 3 Drawing Sheets

METHOD OF DRYING CELLS FOR SCANNING ELECTRON MICROSCOPY

TECHNICAL FIELD

The present invention relates, in general, to a method of drying biological specimens, such as animal cells or other animal tissue samples (including human cells or human tissues), so as to preserve their surface ultrastructure for examination or imaging by electron microscopy, preferably scanning electron microscopy. More particularly, the present invention relates to an improved method of air drying the specimens with a fluorocarbon fluid that does not deplete the earth's protective ozone layer, and preferably also is non-flammable.

RELATED ART

Scanning electron microscopy (hereinafter, abbreviated as SEM) has long been employed during research and/or pathology diagnosis for examining and imaging very small samples, i.e. cells or tissue samples, having a diameter in the range of micrometers.

In the past, drying of cells or tissues (hereinafter, collectively referred to as biological specimens or biological samples) to prepare them for SEM has been done by three common techniques, critical point drying, freeze drying, and air drying. Although preservation of the surface ultrastructure of the samples is accomplished with these techniques, all three techniques present limitations.

More particularly, these three techniques, especially critical point drying, use fluids such as FREON® (registered trademark of E. I. Du Pont de Nemours and Company of Wilmington, Del., for various fluorinated carbons, such as $CClF_3$, $CHF_3$, $CCl_2F-CClF_2$, and $CF_3-CF_3$, known as FREON 13, FREON 23, FREON 113, and FREON 116, respectively) for drying of samples. However, as can be seen, many of these FREONs are chloroflourocarbons (hereinafter, abbreviated as CFCs).

If a CFC is employed as the fluid for drying, a hazard arises in that such fluids are detrimental to the earth's protective ozone layer. In connection therewith, CFCs have been designated by the U.S. Government as having an ozone depletion potential (hereinafter, abbreviated as ODP) above 0, some having an ODP as high as 1.

As a result of the ODP problem, the U.S. Government has imposed regulations requiring the phase out of various CFCs for all but certain uses critical to the preservation of human life. Thus, it is important in the drying of biological specimens that suitable substitute materials with an ODP=0 be used.

Specifically, in connection with critical point drying and freeze drying, not only do both of these procedures take a long time to accomplish, but also both require costly instrumentation. Moreover, both of these procedures use high pressure and thus present a risk to the laboratory technician who must take proper safety precautions when performing the procedures. For instance, between the technician and the drying equipment, there should be a shatter resistant window for protection from a pressure explosion causing ruptured equipment parts to fly at the technician. This high pressure risk is especially ominous with the fluid most commonly employed in critical point drying, namely liquid $CO_2$.

More particularly vis-a-vis critical point drying, cell damage becomes a potential problem due to the extraction of cellular components by the fluid and by thermally related pressure stresses. A discussion of these problems from critical point drying, including photographs of dried specimens, can be seen in Cohen, "Critical Point Drying Principles," *Scanning Electron Microsc.*, Vol. II, pp. 303–323 (1979).

Furthermore, freeze drying often causes ice crystal formation, which in turn causes holes in the cell membrane. The holes damage the ultrastructure, whereby the true morphology of the specimen cannot be seen during examination and imaging by SEM. To obviate this problem, the specimen is often infused with a cryoprotectant such as sucrose, glucose, glycerol, ethanol, dimethyl sulfoxide, or dextran to reduce ice crystal formation and damage. However, some of these cryoprotectants do not easily evaporate/sublime and thus remain on the sample, obscuring surface features. A discussion of these problems from freeze drying can be seen in Bozzola and Russell "Specimen Drying Techniques", *Electron Microscopy*, Publishers: Jones & Barlelett, Boston, Mass., chp. 3, pp. 46–50 (1992).

Of the three drying techniques, air drying is the easiest and most rapid method for preparing cells for SEM. Nevertheless, a drawback is that most biological specimens cannot be prepared for SEM by air drying since this procedure causes shrinkage of the specimen. Especially, air drying is the least desirable method for soft biological specimens, such as animal cells, as air drying thereof often results in common artifacts, such as flattening and collapsing of the cells, as well as shrinkage. Hence, such specimens have to be critical point dried or freeze dried, with the problems attendant thereto as discussed above.

Additionally, besides use of FREON as the fluid for drying of samples, the technique involving air drying also uses fluids such as hexamethyldisilazane (hereinafter, abbreviated as HMDS), dimethoxypropane (hereinafter, abbreviated as DMP), or tetramethylsilane (hereinafter, abbreviated as TMS), each of which takes approximately 10 minutes to 1 hour to infuse into the sample and then to evaporate directly from the sample in minutes after the sample is exposed to air. For many specimens, air drying utilizing HMDS, DMP, or TMS gives good structural preservation, although, as noted above, soft biological specimens that are air dried without these fluids often end up with artifacts. However, all of three of HMDS, DMP, and TMS present other drawbacks in that not only are they flammable, but also they are costly.

Moreover, they present problems of adverse health effects to laboratory personnel who contact them with the skin and/or inhale them, as HMDS is corrosive and both of DMP and TMS are irritants. Thus, they can cause problems, such as skin conditions and mucous membrane conditions, to the laboratory personnel.

Furthermore, TMS is hygroscopic. The water taken on by the sample can obscure surface features and thereby prevent viewing the true ultrastructure or morphology of the sample. A discussion of air drying with TMS, including photographs of dried specimens, can be seen in Dey, Baul, Roy, and Dey, "Short Technical Note: A New Rapid Method of Air-Drying for Scanning Electron Microscopy Using Tetramethylsilane", *J. of Micros.*, Vol. 156, Pt. 2, pp. 259–261 (January, 1989). Although Dey, et al. assert in this article that TMS obviates the shrinkage problem typical of air drying techniques, it should be kept in mind that TMS still presents the above-noted problems of flammability, high cost, and irritation.

Lastly, it is noted that a technique for drying biological specimens for scanning electron microcopy, similar to freeze drying and utilizing a sublimation dehydrant, employs a proprietary fluid, PELDRI II®, marketed by Ted Pella, Inc., of Redding, Calif. However, not only does drying with PELDRI II take several hours to perform the SEM, but also drying with PELDRI II presents a risk to the environment as the major component thereof is 1,1,2,2-tetrachloro-1,2-difluoroethane, which is a CFC. Thus, the material does not have an ODP=0.

Hence, it is desirable to find a method of drying biological specimens to prepare them for electron microscopy, particularly SEM, with a fluid that not only allows for the drying to be air drying, as opposed to critical point drying or freeze drying, but also will have an ODP=0.

SUMMARY OF THE INVENTION

Accordingly, the present invention provides a method of air drying biological specimens, such as specimens of cells or tissues from animals, so as to maintain the specimen integrity for examination or imaging by electron microscopy, such as scanning electron microscopy. By the phrase "maintain specimen integrity" is meant preserve the surface ultrastructure of the cell and/or tissue specimens, i.e., preserve their original shapes and sizes.

The method comprises isolating a biological specimen that has been removed from a biological subject, such as an animal, and then placing the specimen on a cover slip. Next, the method comprises fixing and dehydrating the specimen. After that, the method comprises submerging the specimen in a fluid for a time sufficient for the fluid to infuse into the specimen, followed by removing the specimen from the fluid and allowing the specimen to air dry therefrom. Then, the method comprises sputter coating the specimen with a conductive metal.

The method further comprises that allowing the specimen to air dry from the fluid is performed with the fluid being a fluorinated carbon fluid having a low surface tension less than about 10 dynes/cm at 25° C., a low boiling point less than about 35° C., and an ozone depletion potential of 0. As a result of the ozone depletion potential being 0, the inventive method is environmentally safe in that the method is free of adverse effects on the protective ozone layer of the earth.

Either presently or later, electron microscopy may be performed and the specimen on the cover slip is examined and/or imaged with an electron microscope. Suitably, the electron microscopy is scanning electron microscopy and the microscope is a scanning electron microscope. As specimen integrity has been maintained, true morphology or ultrastructure can be viewed or imaged vis-a-vis electron microscopy.

Preferably, in the method of the present invention, allowing the specimen to air dry from the fluid is accomplished with a fluorinated carbon fluid that is also non-flammable. Even more preferably, in addition to the fluorinated carbon fluid being non-flammable, the fluid is substantially inert, i.e., essentially non-reactive with other chemicals and with the tissues with which it comes in contact and also practically non-toxic from inhalation of vapors or ingestion by humans. Thus, unlike HMDS, DMP, and TMS, the fluid, in the preferred embodiment, is free of adverse health effects to laboratory personnel and/or does not subject them to fire hazards.

Most preferably, allowing the specimen to air dry is accomplished with a fluorinated carbon fluid that is a perfluorocarbon fluid, and a suitable perfluorocarbon fluid is available from 3M under the trade name PF-5050. (The empirical formula of PF-5050 is $C_5F_{12}$.)

Thus, an object of the present invention is to provide a method of air drying biological specimens in order to prepare them for electron microscopy, such as scanning electron microscopy, which method employs a fluid that does not have a detrimental effect on the ozone layer of the earth.

It is a further object of the present invention that the method of air drying employs a fluid that does not damage the ultrastructure and cause the biological specimen to end up with artifacts, such as flattening, collapsing, wrinkling, and/or excessive shrinking, that prevent examination or imaging of the true morphology of the specimen vis-a-vis the electron microscopy. This is an especially important advantage when the method is employed for air drying soft biological specimens.

It is advantage of the present invention that the method of air drying employs a fluid that has both a low surface tension and a low boiling point, whereby the biological specimens do not have to be critical point dried or freeze dried, but can be air dried. Thus, obviated is the high pressure/explosion problem of critical point drying and freeze drying.

Some of the objects and advantages of the invention having been stated above, other objects and advantages will become evident as the description proceeds, when taken in conjunction with the laboratory example and accompanying figures as best described below.

DETAILED DESCRIPTION OF THE INVENTION

Figure 1:
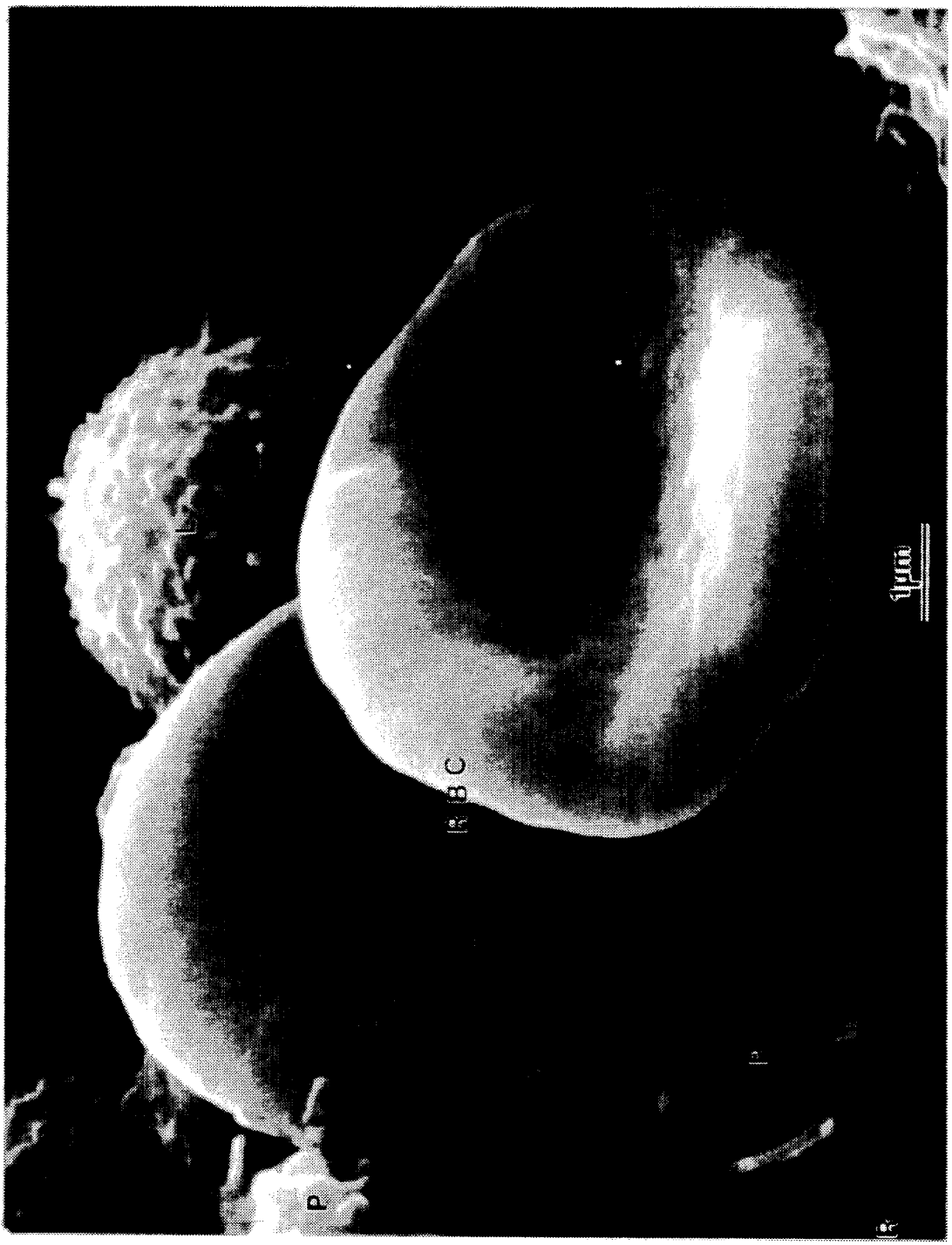
FIG. 1 is a scanning electron micrograph of human red blood cells, both lymphocytes and platelets, that were prepared for SEM using $C_5F_{12}$.

Prior to discussing the laboratory example and micrographs, the following overall comments are provided with respect to the invention.

First, a biological specimen is isolated, placed on a cover slip, fixed, and dehydrated. Then, it is submerged in a fluid and air dried therefrom. Thus, in general, the present invention is a method of air drying biological specimens, such as cells or tissues from animals, in order to prepare them for electron microscopy. Preferably, the invention is intended to be employed in combination with scanning electron microscopy.

The invention employs a fluid that allows for biological specimens to be air dried, therefore obviating the problems of critical point drying and/or freeze drying of specimens in their preparation for scanning electron microscopy.

The specimen is kept submerged in the fluid, typically for about 3 to 15 minutes, more preferably about 5 to 13 minutes, most preferably about 10 minutes to allow the fluid to infuse therein. Then, the specimen is removed from the fluid—either the specimen can be pulled out of the fluid or the fluid can be drained off the specimen. Next, the fluid-treated specimen is allowed to air dry, typically for about 0.5 to 2.5 minutes, more preferably about 0.7 to 1.5 minutes, most preferably about 1 minute, as the remainder of the fluid evaporates therefrom, and usually, the air drying is performed around room temperature, i.e., at a temperature from 20° C. to 25° C.

After the air drying, the specimen is mounted on a specimen mount and sputter coated with conductive metal, usually a combination of gold and palladium. Finally, the specimen may be viewed with an electron microscope, or stored and viewed later.

The inventive method results in the air dried specimen being free of having artifacts, such as flattening, collapsing, wrinkling, or excessive shrinking that interfere with examination or imaging vis-a-vis the electron microscope.

Employed for the air drying fluid is a fluorinated carbon fluid that has an ODP=0 and therefore does not present the ozone depletion problem of the prior art FREON employed in the drying of specimens. Preferably, the fluorinated carbon fluid is also non-flammable and therefore does not present the fire hazard problem of the prior art HMDS, DMP, and TMS employed in the drying of specimens. Even more preferably, the fluorinated carbon fluid is additionally substantially inert, and therefore does not present the corrosion/irritation problems of the prior art HMDS, DMP, and TMS employed in the drying of specimens. Most preferably, the fluorinated carbon fluid is a perfluorocarbon fluid.

A suitable fluorinated carbon that is non-depleting to the ozone, non-flammable, and substantially inert is a perfluorocarbon fluid available from 3M Industrial Chemical Products Division, St. Paul, Minn., under the trade name PF-5050. 3M sells this and other perfluorocarbon fluids for use in liquid burn-in testing and degreasing of electronic components, as described in the 3M sales brochures "Liquid Burn-In Testing with Fluorinert™ Electronic Fluids" (April, 1993) and "Advanced Vapor Degreasing" (December, 1992).

More particularly in regard to PF-5050, it has an ODP=0 and an average molecular weight of 288. The boiling point is 30° C. and the liquid density at 25° C. is 1.63 g/ml, so that this material is a liquid at room temperature. The surface tension at 25° C. is 9.5 dynes/cm and the vapor pressure at 25° C. is 11.80 psia. The heat of vaporization at the boiling point is 21 cal/g and the solubility of water is 7 ppm by weight at 25° C. PF-5050 has no flash point and is therefore non-flammable. Its Hildebrand solubility parameter is 5.5 and its empirical chemical formula is $C_5F_{12}$. PF-5050 was used in the example below.

Other fluorinated carbon fluids, that are liquid at room temperature and have surface tension and boiling point properties similar to those of PF-5050, are also suitable in the method of the present invention, as long as they additionally have an ODP=0. Thus, these other fluorinated carbon materials should have a low surface tension below about 10 dynes/cm at 25° C. and a low boiling point below about 35° C. Moreover, they preferably should also be non-flammable and also be substantially inert.

Laboratory Example and Detailed Discussion of Figures

The following laboratory example was performed and scanning electron micrographs of the fluid-treated specimens were taken, as an illustration of the desirable results obtained when specimens were air dried with $C_5F_{12}$ (PF-5050 from 3M).

In a sterile environment, human blood cells were isolated from the peripheral blood of healthy volunteers as follows. Whole blood was drawn into a sodium citrate vacutainer (available from Becton Dickinson of Rutherford, N.J.), and then carefully layered over a 1.113 density gradient medium (available from Gibco BRL of Grand Island, N.Y., under the trade name, Polymorphprep™). The resultant was centrifuged for 40 minutes at 450 times gravity in a swing-out rotor at 20° C., which created two bands.

The neutrophils in the lower band were diluted by the addition of an equal volume of 0.5 normal Hepes-buffered Hanks' balanced salt solution (available from Sigma Chemical Co., St. Louis, Mo.) to restore normal osmolality. The cell suspension was then washed and resuspended in Hanks' balanced salt solution. The monocytes and lymphocytes from the upper band were washed with and resuspended in Hanks' balanced salt solution.

Cells were first deposited on 12-mm glass disks previously treated with Cell-Tak (available form Collaborative Biomedical Research of Bedford, Mass.). After two minutes, the cells were fixed with 2.5% glutaraldehyde and 0.1M cacodylate buffer (pH=7.4) for one hour and then post-fixed in 1% $OsO_4$ for another hour in veronal acetate buffer (pH=7.4). Dehydration of the cells was carried out in a graded series of ethanol solution.

Finally, the cells were submerged in $C_5F_{12}$ (PF-5050 from 3M) for 10 minutes. After the submergence, the $C_5F_{12}$ was drained off, and the cells were air dried at room temperature (22° C.) for 1 minute as the remainder of the $C_5F_{12}$ evaporated therefrom.

Next, all specimens were mounted on aluminum stubs using carbon conducting tape and then sputter-coated with a thin layer (approximately 20 nm) of gold-palladium using a Hummel V Sputterer (available from Antech, Limited of Alexandria, Va.). Specimens were then stored under vacuum until they were examined and imaged in a Philips 501 Scanning Electron Microscope at 15 kV.

Figure 2:
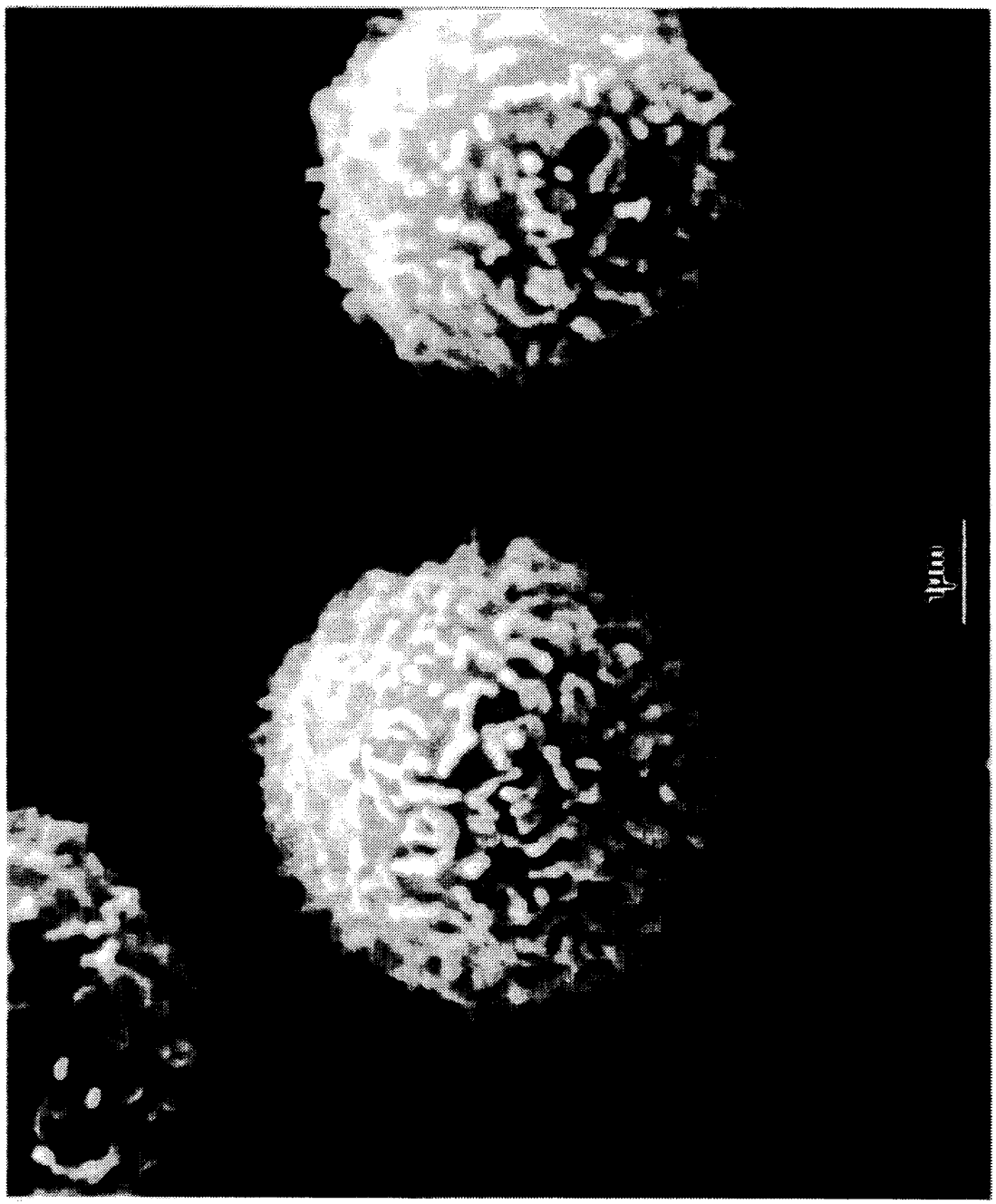
FIG. 2 is a scanning electron micrograph of human lymphocytes prepared for SEM using $C_5F_{12}$.
Figure 3:
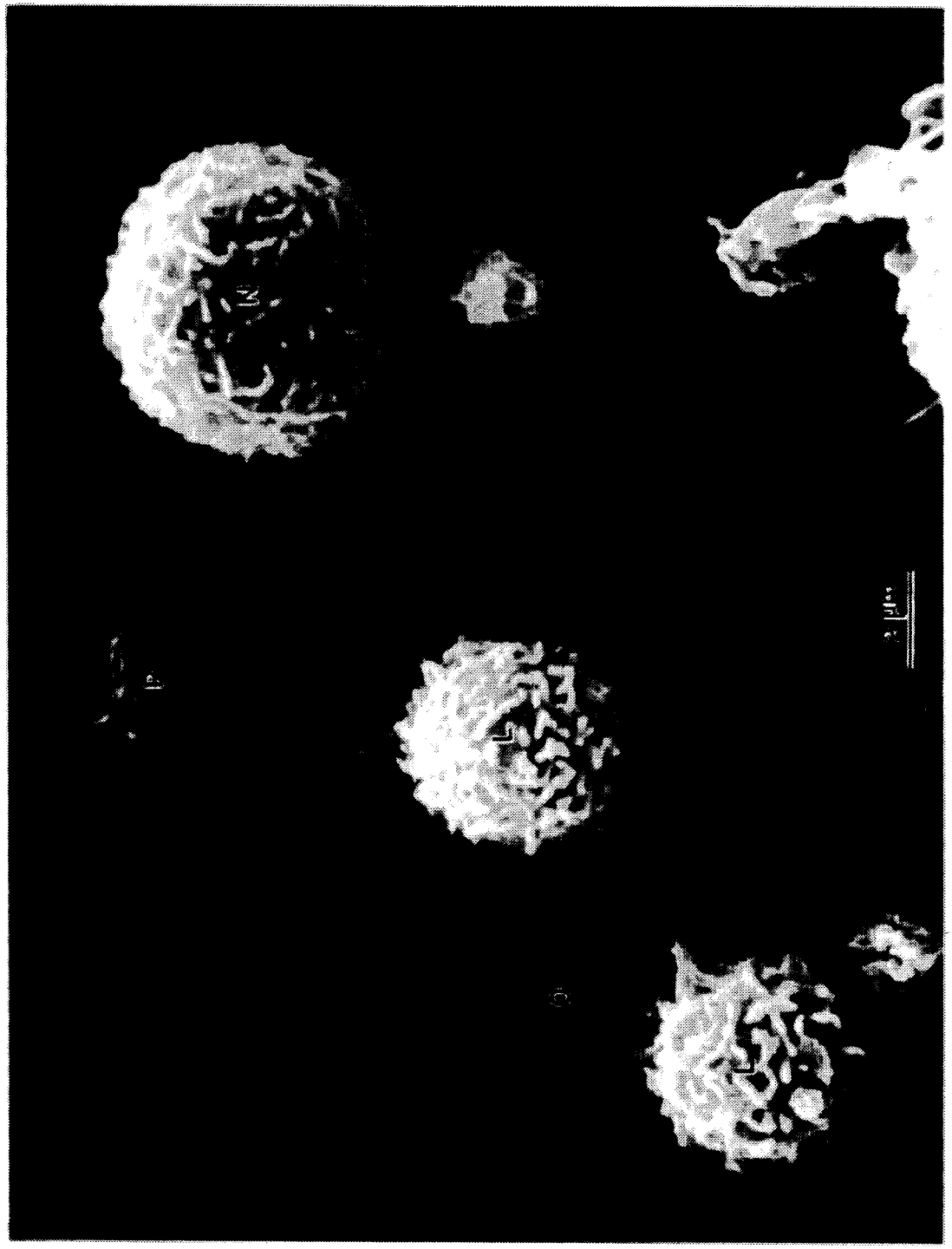
FIG. 3 is a scanning electron micrograph of human neutrophils, lymphocytes, and platelets prepared for SEM using $C_5F_{12}$.

Scanning electron micrographs of the imaged specimens are presented in the accompanying FIGS. 1, 2, and 3. The following abbreviations are used in the micrographs, with the letter(s) being printed directly on the particular type of cell to indicate what kind of cell it is:

| | |
|---|---|
| Red Blood Cells | RBC |
| Lymphocytes | L |
| Platelets | P |
| Neutrophils | N |

These cells are very small in size. The size can be determined by the comparative indication of a distance of 1 micrometer (FIGS. 1 and 2) or 2 micrometers (FIG. 3) designated at the bottom-center of the micrographs.

More particularly, there can be seen in FIG. 1 human red blood cells, both lymphocytes and platelets, that were prepared with $C_5F_{12}$ for SEM. The quality is excellent from these cells treated with $C_5F_{12}$.

FIG. 2 is a scanning electron micrograph of human lymphocytes that were prepared with $C_5F_{12}$ for SEM. Like the cells in the micrograph in FIG. 1, the cells in the micrograph in FIG. 2 are of excellent quality.

FIG. 3 shows a scanning electron micrograph of human neutrophils, lymphocytes, and platelets, that were also prepared for SEM using $C_5F_{12}$. Again, the quality of these cells is excellent, just as the quality of the cells in FIGS. 1 and 2.

The scanning electron micrographs show that the surface morphologies of blood cells that were air dried from $C_5F_{12}$, in accordance with the laboratory example above, are indistinguishable from the surface morphologies of cells that were critical point dried, such as by the procedure discussed in the above-mentioned article by Cohen, or from the surface morphologies of cells that were air dried, such as by the procedure discussed in the above-mentioned article by Dey, Baul, Roy, and Dey. As can be seen in the accompanying Figures, even the most delicate cell structures, such as the surface microvilli, show no evidence of distortion or collapse.

Thus, $C_5F_{12}$ as a fluid for drying cells or tissues to prepare them for scanning electron microscopy can be effectively used in a method of air drying the cells or tissues in place of prior art fluids that are used for drying to prepare cells or tissues for scanning electron microscopy. Moreover, as compared to prior art fluids, $C_5F_{12}$ has the additional advantages of being fast, being economical, being non-flammable, having no adverse health effects for laboratory personnel, being environmentally safe with an ODP=0, being stable with a long shelf life at room temperature, and not producing artifacts.

It will be understood that various details of the invention may be changed without further departing from the scope of the invention. Furthermore, the foregoing description is for the purpose of illustration only, and not for the purpose of limitation—the invention being defined by the claims.

What is claimed is:

1. A method of air drying biological specimens so as to maintain specimen integrity for scanning electron microscopy examination or imaging, said method comprising the steps of:

(a) isolating a biological specimen that has been removed from a biological subject;

(b) placing the specimen on a cover slip;

(c) fixing and dehydrating the specimen;

(d) submerging the specimen in a fluorinated carbon compound fluid for a sufficient time for the fluid to infuse into the specimen, said fluid having a low surface tension less than about 10 dynes/cm at 25° C., a low boiling point less than about 35° C., and an ozone depletion potential of 0;

(e) removing the specimen from the fluid;

(f) allowing the specimen with the fluid to air dry; and (g) sputter coating the specimen with a conductive metal;

whereby said method is environmentally safe in that said method is free of adverse effects on the protective ozone layer of the earth.

2. The method of claim 1, wherein the biological specimen is selected from the group consisting of an animal cell, and an animal tissue.

3. The method of claim 1, wherein the biological specimen is a soft biological specimen.

4. The method of claim 1, wherein the step of the submerging of the biological specimen in the fluorinated carbon fluid is for about 3 to about 15 minutes.

5. The method of claim 4, wherein the step of the submerging of the biological specimen in the fluorinated carbon fluid is for about 10 minutes.

6. The method of claim 1, wherein the step of the air drying is for about 0.5 to about 2.5 minutes.

7. The method of claim 6, wherein the step of the air drying is for about 1 minute.

8. The method of claim 1, wherein the step of the air drying is at a temperature from about 20° C. to about 25° C.

9. The method of claim 1, wherein the step of the allowing the biological specimen to air dry from the fluorinated carbon fluid results in the air dried specimen being free of having artifacts that interfere with electron microscopy examination or imaging.

10. The method of claim 9, wherein the biological specimen is a soft biological specimen.

11. The method of claim 1, wherein the step of the allowing the specimen to air dry from the fluid is accomplished with the fluorinated carbon fluid being substantially inert, whereby the method is free of adverse health effects to a person performing the method.

12. The method of claim 1, wherein the step of the allowing the specimen to air dry from the fluid is accomplished with the fluorinated carbon fluid being non-flammable, whereby the method is free of explosion/fire hazards to a person performing the method.

13. The method of claim 1, wherein the step of the allowing the specimen to air dry from the fluid is accomplished with the fluorinated carbon fluid being a perfluorocarbon fluid.

14. The method of claim 1, wherein the step of the allowing the specimen to air dry from the fluid is accomplished with the fluorinated carbon fluid being $C_5F_{12}$.

15. The method of claim 1, further including the step of examining or imaging the specimen on the cover slip with an electron microscope.

* * * * *